US010392999B2

(12) United States Patent
Zhang

(10) Patent No.: US 10,392,999 B2
(45) Date of Patent: Aug. 27, 2019

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 287 days.

(21) Appl. No.: 15/290,893

(22) Filed: Oct. 11, 2016

(65) Prior Publication Data
US 2018/0100424 A1 Apr. 12, 2018

(51) Int. Cl.
*F01N 11/00* (2006.01)
*F01N 13/00* (2010.01)
*G01N 15/06* (2006.01)
*G01N 15/00* (2006.01)

(52) U.S. Cl.
CPC ............ *F01N 11/00* (2013.01); *F01N 13/008* (2013.01); *G01N 15/0606* (2013.01); *G01N 15/0656* (2013.01); *F01N 2560/05* (2013.01); *F01N 2560/20* (2013.01); *G01N 2015/0046* (2013.01); *Y02T 10/47* (2013.01)

(58) Field of Classification Search
CPC ............ F01N 2560/05; G01N 15/0606; G01N 15/0656
See application file for complete search history.

(56) References Cited

U.S. PATENT DOCUMENTS

| 4,199,424 A * | 4/1980 | Teitelbaum | G01N 27/4077 204/428 |
| 4,929,331 A * | 5/1990 | Kato | G01N 27/4077 204/426 |
| 6,780,298 B2 * | 8/2004 | Nakamura | G01N 27/4077 204/428 |
| 7,739,898 B2 * | 6/2010 | Shaddock | F01N 13/08 73/23.31 |
| 7,758,736 B2 * | 7/2010 | Okumura | G01N 27/4077 204/424 |
| 7,901,556 B2 * | 3/2011 | Yamada | G01N 27/4077 204/424 |
| 8,211,293 B2 * | 7/2012 | Nishijima | G01N 33/0037 205/781 |
| 8,225,648 B2 * | 7/2012 | Nelson | G01N 15/0656 73/114.71 |
| 8,310,249 B2 | 11/2012 | Paterson | |
| 8,413,483 B2 * | 4/2013 | Yamada | G01N 27/4077 204/428 |
| 8,915,119 B2 * | 12/2014 | Ueno | F01N 9/002 73/23.33 |
| 8,966,956 B2 * | 3/2015 | Yoshioka | F01N 13/008 73/23.33 |
| 9,003,866 B2 * | 4/2015 | Tsuzuki | G01N 27/4077 204/424 |
| 9,778,160 B2 * | 10/2017 | Zhang | G01N 15/0656 |
| 9,791,426 B2 * | 10/2017 | Ebelsberger | G01N 1/2226 |

(Continued)

*Primary Examiner* — John Fitzgerald
(74) *Attorney, Agent, or Firm* — Julia Voutyras; McCoy Russell LLP

(57) ABSTRACT

Methods and systems are provided for a particulate matter sensor positioned downstream of a diesel particulate filter in an exhaust system. In one example, a particulate matter sensor may include a cylindrical assembly with a circular plate and a plurality of dividers located therein.

11 Claims, 8 Drawing Sheets

(56) References Cited

U.S. PATENT DOCUMENTS

| | | | | |
|---|---|---|---|---|
| 9,816,426 B2* | 11/2017 | Zhang | ............ | F01N 13/008 |
| 9,841,357 B2* | 12/2017 | Zhang | ............ | G01M 15/102 |
| 10,024,260 B2* | 7/2018 | Zhang | ............ | G01N 15/0606 |
| 10,048,188 B2* | 8/2018 | Zhang | ............ | G01N 15/0656 |
| 10,078,043 B2* | 9/2018 | Zhang | ............ | G01M 15/102 |
| 2002/0053233 A1* | 5/2002 | Grieser | ............ | G01K 13/02 |
| | | | | 73/31.05 |
| 2002/0195339 A1* | 12/2002 | Nakamura | ............ | G01N 27/4077 |
| | | | | 204/428 |
| 2012/0085146 A1 | 4/2012 | Maeda et al. | | |
| 2012/0111092 A1* | 5/2012 | Nakashima | ............ | G01N 27/4077 |
| | | | | 73/23.31 |
| 2012/0186330 A1* | 7/2012 | Ueno | ............ | F01N 9/002 |
| | | | | 73/23.33 |
| 2013/0031952 A1* | 2/2013 | Day | ............ | G01N 27/4077 |
| | | | | 73/23.31 |
| 2015/0075253 A1* | 3/2015 | Boyd | ............ | G01N 33/0036 |
| | | | | 73/23.31 |
| 2015/0101394 A1* | 4/2015 | Fujita | ............ | G01N 27/4077 |
| | | | | 73/23.31 |
| 2015/0192509 A1* | 7/2015 | Brueck | ............ | G01N 33/0011 |
| | | | | 73/23.31 |
| 2015/0355066 A1* | 12/2015 | Zhang | ............ | G01N 15/0656 |
| | | | | 73/23.31 |
| 2015/0355067 A1* | 12/2015 | Zhang | ............ | G01N 15/0656 |
| | | | | 73/23.31 |
| 2016/0003789 A1* | 1/2016 | Ebelsberger | ............ | G01N 1/2226 |
| | | | | 60/722 |
| 2017/0058746 A1 | 3/2017 | Zhang | | |
| 2017/0159536 A1* | 6/2017 | Uchiyama | ............ | F01N 3/023 |
| 2017/0261417 A1* | 9/2017 | Zhang | ............ | G01M 15/102 |
| 2017/0342923 A1* | 11/2017 | Zhang | ............ | G01N 15/0606 |

* cited by examiner

METHOD AND SYSTEM FOR EXHAUST PARTICULATE MATTER SENSING

FIELD

The present application relates to sensing particulate matter in an exhaust system.

BACKGROUND/SUMMARY

Engine emission control systems may utilize various exhaust sensors. One example sensor may be a particulate matter sensor, which indicates particulate matter mass and/or concentration in the exhaust gas. In one example, the particulate matter sensor may operate by accumulating particulate matter over time and providing an indication of the degree of accumulation as a measure of exhaust particulate matter levels. The particulate matter sensor may be located upstream and/car downstream of a diesel particulate filler, and may be used to sense particulate matter loading on the particulate filter and diagnose operation of the particulate filter.

One example of a PM sensor is shown by Maeda et. al. in US 20120085146 A1. Therein, the particulate matter sensor is attached to the top of an exhaust pipe and housed within a cylindrical protection tube. The PM sensor additionally includes a sensor element that is positioned closer to a center of the exhaust pipe so that the sensor output more reasonably represents an average soot concentration in the exhaust pipe. In addition, the PM sensor includes inlet apertures configured to direct the exhaust into the sensor and towards the sensor element. Herein, the sensor element is positioned closer to the inlet holes to allow the sensor element to capture more of the incoming particulates.

However, the inventors have recognized potential issues with such sensor configurations. As one example, such an arrangement may make the sensor element more vulnerable to being contaminated by water droplets in the exhaust condensing at or near the inlet apertures. In such sensor configurations, additional protective coating may be required to protect the soot sensor element from direct impingement of larger particulates and wa ter droplets. Adding additional protective layer may reduce the electrostatic attraction between the charged soot particles and the electrodes of the sensor element and may lead to reduced soot sensor sensitivity. With reduced sensitivity, the soot sensor may not be able to determine the leakage of the particulate filter in a reliable way. Thus, errors in the sensor may lead to a false indication of DPF degradation and unwarranted replacement of functioning filters.

On the other hand, if the sensor is mounted at the bottom of the exhaust pipe, as shown by Paterson in U.S. Pat. No. 8,310,249 B2, water condensing at the bottom of the exhaust pipe may overflow into the sensor element thereby contaminating the sensor element. Such contamination of the sensor element may lead to fluctuations in the output of the sensor, thereby decreasing the accuracy of estimating particulate loading on the particulate filter.

The inventors herein have recognized the above issues and identified an approach to at least partly address the issues. In one example approach, a particulate matter sensor assembly comprising a cylindrical assembly, an inner device positioned within an outer device of the cylindrical assembly with a radius less than a radius of the outer device, and a sensor element located above an annular space proximal to a dome located at a top end of the outer device. In this way, by positioning the sensor element above the annular space, issues related to water droplets and larger contaminants impinging on the sensor element and causing fluctuations in the sensor output may be reduced.

As one example, an exhaust particulate matter sensor assembly may be positioned downstream of an exhaust particulate filter in an exhaust pipe. The particulate matter sensor may include a cylindrical assembly including perforations located at a bottom end, and a sensor element positioned at a top end of the assembly, with the inner device located between the two. The cylindrical assembly further includes an interior flow space divided into equal portions via a plurality of dividers, and where each of the divided portions includes at least one perforation of the perforations. A dome is located at the top end of the assembly and extends outside of the exhaust passage.

The perforations fluidly couple the interior flow space to the exhaust passage. As such, exhaust gas flows through the perforations to enter and exit the cylindrical assembly. The inner device is radially smaller than the cylindrical assembly. As such, a small annular space exists between the circumference of the inner device and an inner surface of the outer device. The sensor element is positioned on surfaces of the dividers, with oppositely charged electrodes of the sensor element being located on alternating divider surfaces. By doing this, exhaust gas flows over the sensor element, into the dome where the exhaust gas is scrambled and redirected to different divided portions, and back over the sensor element. This may provide more uniform particulate deposition across surfaces of the sensor element.

In this way, the functioning of the sensor element may be improved and the sensor may be rendered more reliable. In addition, by enabling a more accurate diagnosis of the exhaust particulate filter, exhaust emissions compliance may be improved. This reduces the high warranty costs of replacing functional particulate filters. The exhaust may exit the sensor via the perforations. The symmetrical design of the cylindrical assembly and inner device eliminate manufacture process for specific sensor orientation at the installation and enhance the sensor repeatability.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2-4 are shown approximately to scale.

DETAILED DESCRIPTION

Figure 1:
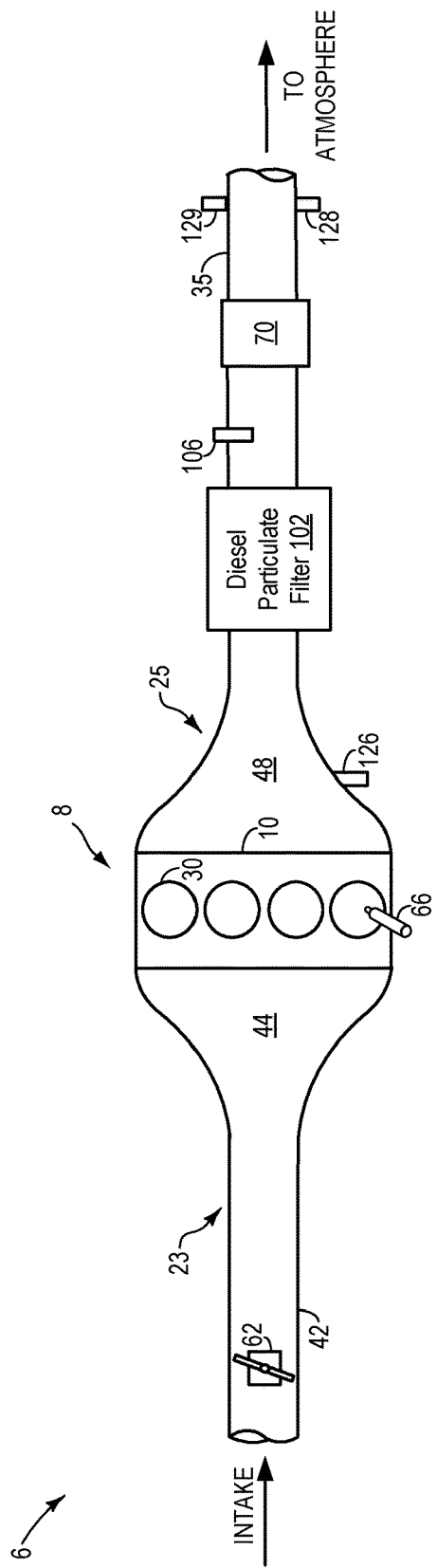
FIG. 1 shows a schematic diagram of an engine and an associated particulate matter (PM) sensor positioned in an exhaust flow.
Figure 2:
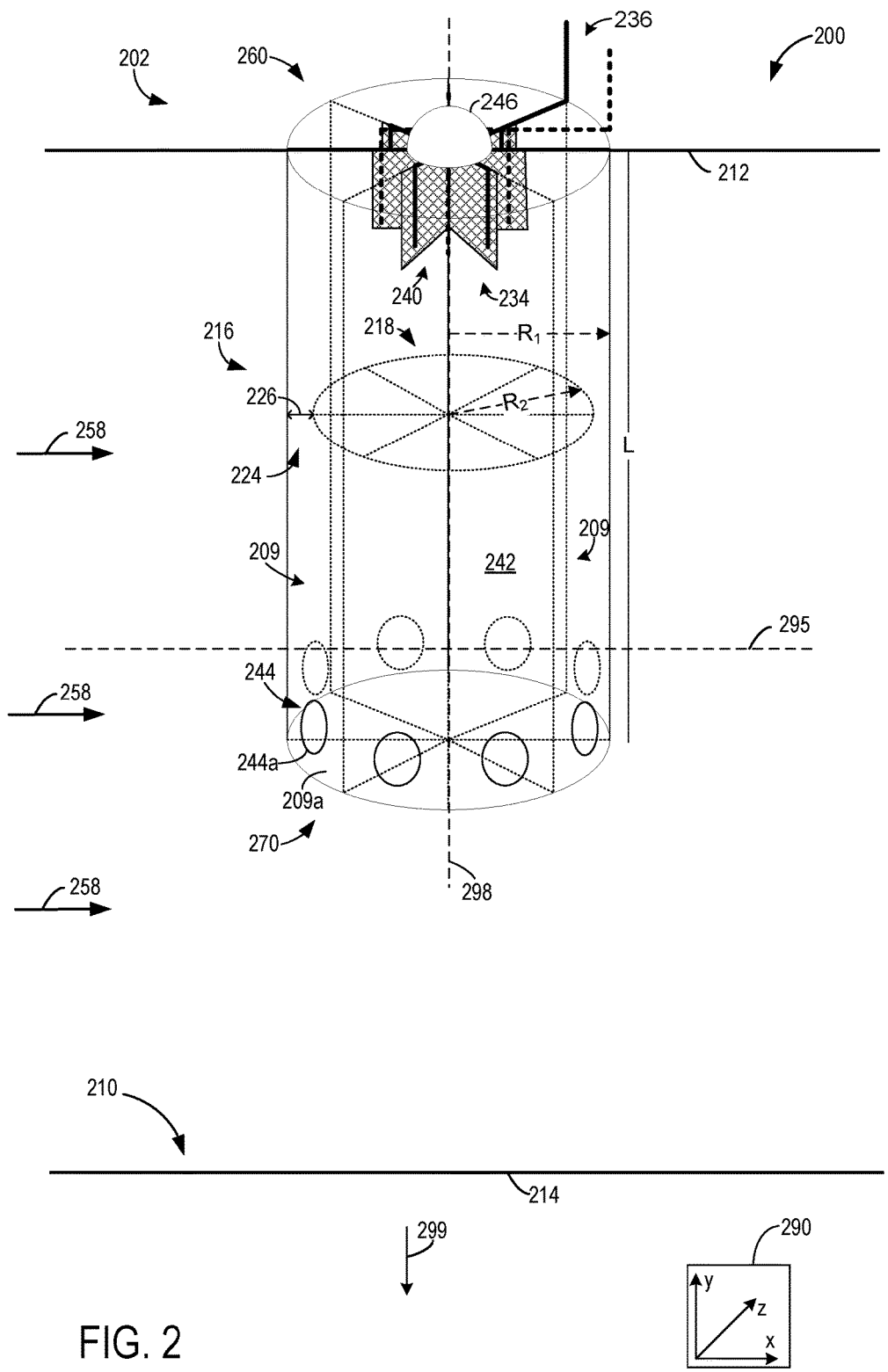
FIG. 2 shows a schematic diagram of the PM sensor including a cylindrical assembly having a plurality of perforations fluidly coupling compartments of an interior flow space to an exhaust passage.
Figure 3:
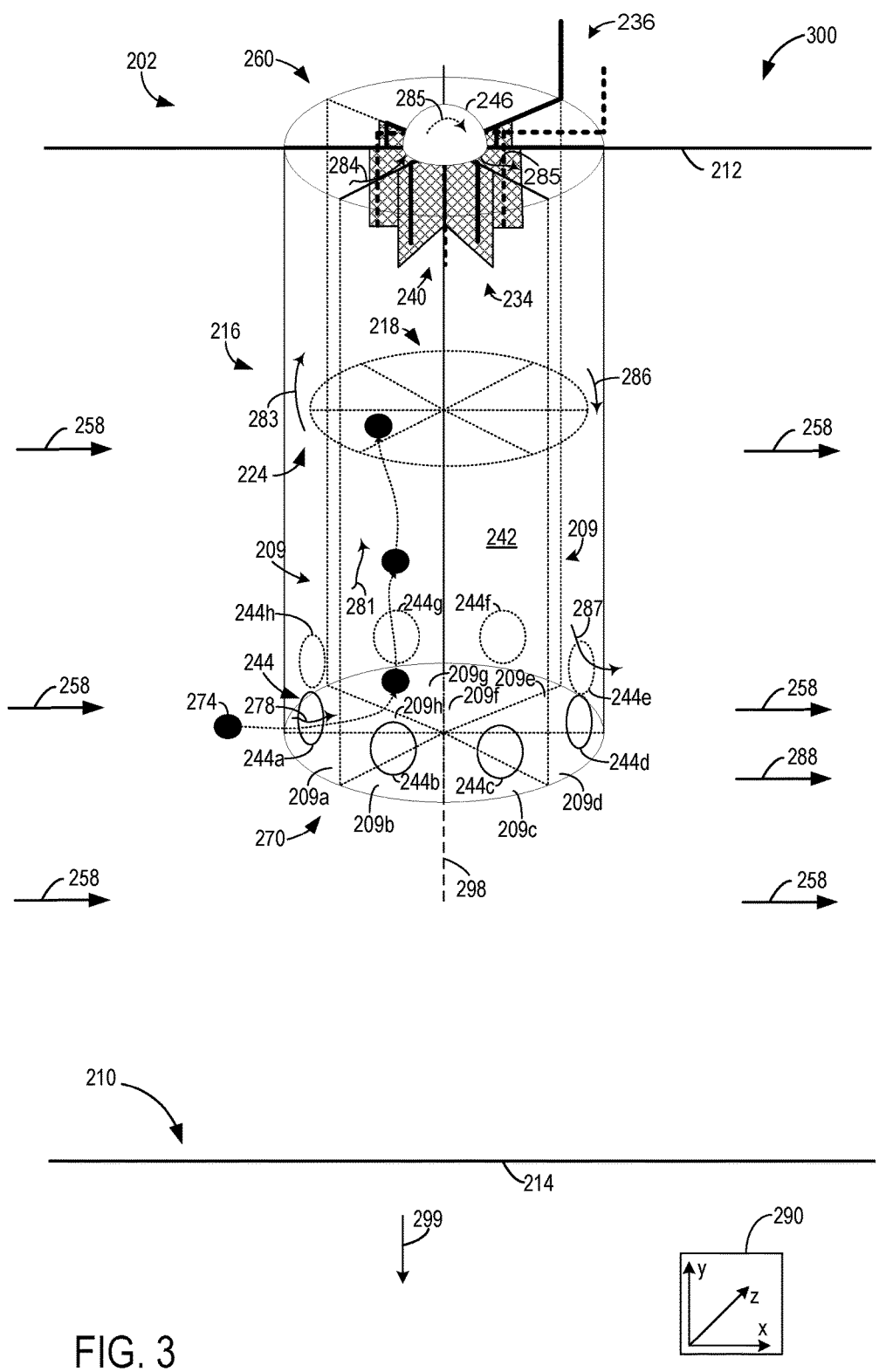
FIG. 3 shows a schematic diagram of the PM sensor showing exhaust flowing into the PM sensor via perforations at a bottom of the PM sensor.
Figure 4:
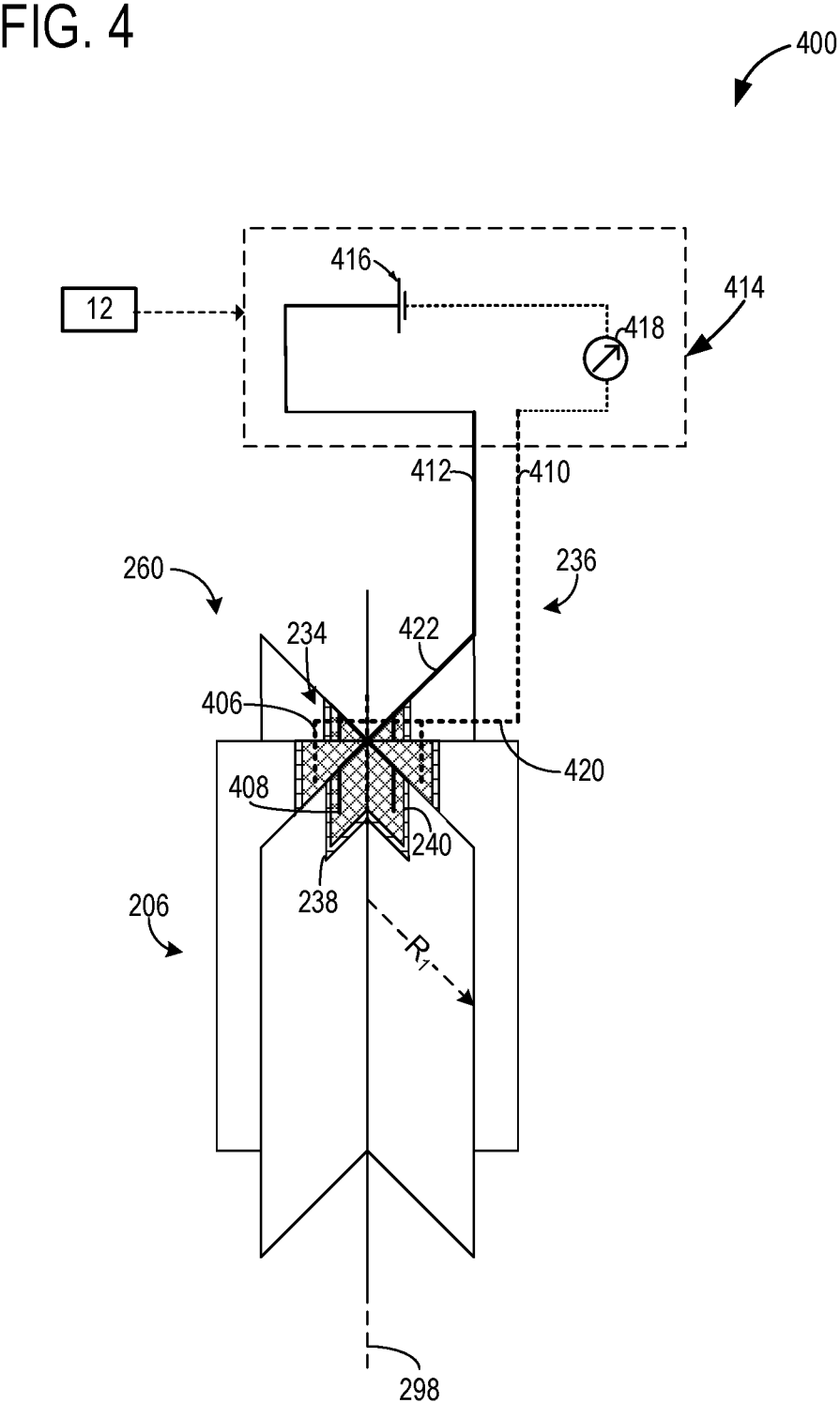
FIG. 4 shows an example layout of electrodes formed on first surfaces of the sensor element.

The following description relates to systems and methods for sensing particulate matter (PM) in an exhaust flow of an engine system, such as the engine system shown in FIG. 1. A PM sensor may be placed in an exhaust passage of the engine system. The PM sensor may include a cylindrical assembly including a plurality of perforations fluidly coupling an interior flow space to the exhaust passage. The cylindrical assembly may be coupled to a top of the exhaust passage with the perforations being located adjacent to a central axis of the exhaust passage. The interior flow space may be divided into equally sized compartments, each comprising at least one of the perforations. The cylindrical assembly further includes an inner device located between a sensor element and the perforations inside an outer device, as shown in FIG. 2. The perforations function as inlets and outlets of the cylindrical assembly as shown in FIG. 3. The sensor element may include electrodes formed on a first surface of the sensor element as shown in FIG. 4. Additionally, the sensor element may include heating elements formed on a second, surface opposite the first as shown in FIG. 4. A controller may be configured to perform a control routine, such as an example routine of FIG. 5 to accumulate particulates in the exhaust across the electrodes of the sensor element. Further, the controller may intermittently clean the PM sensor (FIG. 6) to enable continued PM monitoring. Furthermore, the controller may be configured to perform a routine, such as an example routine of FIG. 7 to regenerate the exhaust particulate filter based on a time between PM sensor regenerations. An example of filter diagnostics is shown in FIG. 8. In this way, the functioning of the PM sensor to estimate the filtering capabilities of the DPF (and thereby to detect DPF leaks) may be increased.

FIGS. 1-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. As an example, while operating the PM sensor to accumulate soot particulates, the controller may send a control signal to an electric circuit to apply a voltage to the sensor electrodes of the PM sensor to trap the charged particulates onto the surface of the sensor electrodes. As another example, during PM sensor regeneration, the controller may send a control signal to a regeneration circuit to close a switch in the regeneration circuit for a threshold time to apply a voltage to heating elements coupled to the sensor electrodes to heat the sensor electrodes. In this way, the sensor electrodes are heated to burn off soot particles deposited on the surface of the sensor electrodes. Example routines are described herein with reference to FIGS. 5-7.

Turning now to FIG. 2, a schematic view 200 of an example embodiment of a particulate matter (PM) sensor assembly 202 (such as PM sensor 106 of FIG. 1) is shown. The PM sensor assembly 202 may be configured to measure PM mass and/or concentration in the exhaust gas, and as such, may be coupled to an exhaust passage 210 (e.g., such as the exhaust passage 35 shown in FIG. 1), upstream or downstream of a diesel particulate filter (such as DPF 102 shown in FIG. 1). Portions of the PM sensor assembly 202 depicted in dashed lines are occluded by portions of the figure in solid line.

An axis system 290 comprising three axes, namely an x-axis parallel to the horizontal direction, a y-axis parallel to the vertical direction, and a z-axis perpendicular to both the x- and y-axes, is shown. A direction of gravity 299 is shown with an arrow parallel to the vertical direction. A central axis 295 of the exhaust passage 210 is shown parallel to the horizontal direction. An axial axis 298, which may also be used as a central axis 298 of the PM sensor assembly 202, is perpendicular to the central axis 295.

In the schematic view 200, the PM sensor assembly 202 is disposed inside the exhaust passage 210 with exhaust gases flowing (in a horizontal direction along the X-axis) from downstream of the diesel particulate filter towards an exhaust tailpipe, as indicated by arrows 258. The PM sensor assembly 202 is mounted inside the exhaust passage 210. Herein, the PM sensor assembly 202 is cylindrical in shape. As another example, the assembly may be a hollow elliptical structure positioned within the exhaust passage 210. As shown, the PM sensor assembly 202 is symmetric about the y-axis.

The PM sensor assembly 202 extends along the y-axis in a direction orthogonal to the direction of exhaust gas flow 258. Further, the PM sensor assembly 202 may include a top end 260 and a bottom end 270. A portion of the top end 260 may be coupled to a top 212 (and not coupled to a bottom 214 of the exhaust passage 210, for example) of the exhaust passage 210. Thus, the top end 260 may be similarly shaped (e.g., curved) as the top 212 of the exhaust passage 210. Alternatively, the top end 260 may be flat, with only the circumference of the top end 260 being coupled to the top 212. However, the bottom end 270 freely hangs in the exhaust passage 210 and is not coupled to a surface of the exhaust passage 210. In one example, a length L of the PM sensor assembly 202 extends passed the central axis 295 of the exhaust passage 210. In this way, the bottom end 270 is below the central axis 295 relative to the direction of gravity 299. In some examples, the length L may be substantially equal to a radius of the exhaust passage 210 such that the bottom end 270 reaches and does not extend beyond the central axis 295. The top end 260 may be installed in the top 212 of the exhaust passage 210 in a number of ways. For example, the top end 260 may be inserted, screwed, or held to the top 212 via additional screws or bores (not shown). The top end 260 is in sealing contact with the top 212. As such, exhaust gas 258 does not escape through intersection between the top end 260 and the top 212 to an engine (e.g., engine 10 in the embodiment of FIG. 1) or an ambient atmosphere.

The top 260 and bottom 270 ends are sealed from the exhaust passage 210. As such, exhaust gas does not flow through the top end 260 or the bottom end 270. The top end 260 and bottom end 270 are substantially identical circles. It will be appreciated that the top and bottom ends may be other shapes without departing from the scope of the present disclosure, for example, square-shaped. As a result, the PM sensor assembly 202 comprises an outer device 216 located between and sealingly coupled to the top 260 and bottom 270 ends. The outer device 216 is a cylinder with length L. It will be appreciated that the outer device 216 may be other suitable shapes (e.g., spherical, cubical, rectangular prism-like, etc.) without departing from the scope of the present disclosure. In this way, the PM sensor assembly 202 may also be referred to as a cylindrical assembly having a cylindrical outer device 216 coupled to an exhaust pipe of the exhaust passage 210.

An inner device 218 is circular and located inside the outer device 216. The inner device 218 may be comprised of a material substantially identical to a material of the outer device 216. By doing this the inner 218 and outer 216 devices are both impervious to exhaust gas flow. The material may be metal, plastic, alloy, or a combination thereof. The inner device 218 is similar in shape and material to the top 260 and bottom 270 ends, except that its diameter is smaller than the diameters of the top 260 and bottom ends 270 such that a flow space exists between the inner device 218 and the outer device 216, as will be described below.

The outer device 216 is a cylindrical protection device of radius $R_1$. However, the inner device 218 is a circular protection device a radius $R_2$. The radii $R_1$ and $R_2$ are measured from the axial axis 298, which traverses through geometric centers of the top 260 and bottom 270 ends. Herein, the inner device 218 is smaller than the outer device 216 (e.g., $R_2 < R_1$), and an annular gap 224 and/or annular space 224 is located between the outer 216 and inner 218 devices. Thus, the inner device 218 is spaced away from interior surfaces of the outer device 216. The annular gap 224 is uniform between the outer 216 and inner 218 devices, with a gap 226 indicating width of the annular gap 224. In this way, the inner device 218, outer device 216, and the top 260 and bottom 270 ends comprise centers aligned along the axial axis 298. The inner device 218 is asymmetrically located in the outer device 216 such that it is more proximal to the top end 260 compared to the bottom end 270. In other embodiments, the inner device 218 may be symmetrically located in the outer device 216 exactly in the middle of the top 260 and bottom 270 ends. Both the outer 216 and inner 218 devices are fixed and do not slide, rotate, or actuate.

As an example, the length of the PM sensor assembly 202 may be selected such that the bottom end 270 may not extend beyond the central axis 295. In this way, by positioning the sensor assembly 202 close to the central axis 295 of the exhaust passage 210, the average soot particulate concentration in the exhaust passage 210 may be reasonably represented in the sensor assembly. Additionally or alternatively, the PM sensor assembly 202 comprises a plurality of perforations 244 equally spaced around the outer device 216 adjacent the bottom end 270. In some examples, the bottom end 270 may extend below the central axis 295 such that the perforations 244 are located along the central axis 295. At any rate, the sensitivity of the PM sensor assembly 202 may be increased and the sensor may be rendered more reliable. In addition, by enabling a more accurate diagnosis of the exhaust particulate filter, exhaust emissions compliance may be improved. As such, this reduces the high warranty costs of replacing functional particulate filters, exhaust emissions are improved, and exhaust component life is extended.

As shown, each of the top end 260, bottom end 270, and inner device 218 are parallel to the direction of exhaust gas flow 258. The inner device 218 is fixed within and spaced away from interior surfaces of the outer device 216. The inner device 218 is fixedly coupled within the outer device 216 via a plurality of dividers 206. In some examples, the inner device 218 is located within the outer device 216 via a plurality of stand-offs. As shown, there are eight dividers 206 dividing an interior flow space 242 of the outer device 216 into eighths. The dividers 206 are of substantially equal height and width, intersecting along the axial axis 298 and/or geometric center of the outer device 216. The dividers 206 traverse from the top end 260 to the bottom end 270 and are pressed against an interior surface of the outer device 216 for the entire length L of the outer device 216. Said another way, the dividers 206 are located inside of the outer device 216, the dividers are physically coupled to the outer device 216 along their outer edge while being physically coupled to each other along their inner edges intersecting at the axial axis 298, and where the inner device 218 is mounted inside the outer device 216 via the dividers 206. As such, portions of the interior flow space 242 located between first and second dividers of the dividers 206 are fluidly separated from portions of the interior flow space 242 located between second and third dividers. Herein, portions of the interior flow space 242 located between dividers may be referred to as compartments 209 and/or flow sections 209. Each compartment of the compartments 209 is fluidly separated from an adjacent compartment, wherein each compartment of the compartments 209 is substantially equal in volume. Each compartment of the compartments 209 comprises at least a perforation of the perforations 244. In one example, each compartment of the compartments 209 comprises exactly one perforation of the perforations 244. Thus, there are exactly eight perforations 244 located along a common plane facing radially outward directions, in one example. The perforations 244 are substantially identical to each other, wherein each of the perforations 244 is a circle. However, the perforations 244 may be oblong, square, or other suitable shapes for admitting and discharging exhaust gas from the PM sensor assembly 202.

The perforations 244 are equally spaced around the outer device 216 adjacent the bottom end 270 and are configured to introduce exhaust gas to and expel exhaust gas from the PM sensor assembly 202. Specifically, each perforation of the perforations 244 function as an inlet and an outlet for an individual compartment of the compartments 209. For example, perforation 244a is the inlet and outlet for compartment 209a. Thus, the perforation 209a allows exhaust gas to flow only into compartment 209a. Furthermore, exhaust gas in the compartment 209a may only flow from the compartment 209a to the exhaust passage 210 via the perforation 244a.

During cold start of the vehicle, the exhaust may not be warm enough to convert water inside the exhaust pipe into steam (gaseous state), and thus water may continue to remain in the liquid state. By mounting the inner device 218 in the outer device 216, the sensor may be protected from water droplets and/or large particulates due to the gap 226 being smaller than water droplets and/or large particulates. This may prevent and/or reduce large particulates from flowing to a sensor element 234 located at the top end 260 of the outer device 216 adjacent a dome 246. Exhaust gas may swirl in the dome 246 and flow to a compartment different than a compartment from which it came. Said another way, a first compartment may flow exhaust gas into the dome 246 and the exhaust gas may flow into a second compartment, different than the first compartment, from the dome 246. Thus, the dome 246 is a hollow half-sphere with a geometric center aligned with the axial axis 298. In this way, the dome 246 is located above the intersection between the dividers 206. The dome 246 protrudes through a cut-out of the top 212 of the exhaust passage 210 such that exhaust gas in the dome 246 is completely outside the exhaust passage 210. The dome 246 is completely sealed preventing exhaust gas from flowing out the dome 246 to an engine and/or an ambient atmosphere.

The sensor element 234 is coupled to the dividers 206 near the dome 246. The sensor element 234 is located downstream of the gap 226 of the annular space 224 relative to a direction of exhaust gas flow in the PM sensor assembly 202, which is substantially parallel to the axial axis 298. Said another way, the inner device 218 is located between the perforations 244 and the sensor element 234.

The sensor element 234 includes a substrate 240 (shown with a crisscross pattern) having electrodes 236 formed on a first surface, and a heating element (shown in FIG. 4) formed on a second, opposite surface. Said another way, the electrodes 236 and the heating element are formed on two opposite sides of the substrate 240, thus separated by a thickness of the substrate 240. As such, the sensor element 234 may be a square element to take advantage of the flat shape of the dividers 206. However, the sensor element 234 may be rectangular, circular, triangular or the like without deviating from the scope of the present disclosure. For a square shaped element 234, the electrodes 236 may be linear. Various other geometries may alternatively be possible without deviating from the scope of the disclosure. Oppositely charged electrodes are shown in solid and dashed lines. As shown, a divider of the dividers 206 does not comprise both types of electrodes 236. For example, a positive electrode is located on a first divider and dividers directly adjacent the first divider comprise negative electrodes. Thus, the dividers 206 alternate between comprising positive and negative electrodes. In some examples, individual dividers of the dividers 206 may comprise both positive and negative electrodes. As such, the electrodes 236 may be interdigitated in a comb-like structure. However, it will be appreciated that the electrodes may be spiral shaped or other suitable shapes for determining soot in exhaust flow. The soot particulates in the exhaust may be deposited between the interdigitated electrodes as explained with reference to FIG. 4.

The sensor element 234 may be positioned inside the outer device 216 above the inner device 218 such that the electrodes 236 are facing compartments 209 while the heating element that is formed on the opposite surface is pressed against dividers 206. The sensor element 234 is located on both sides of a divider of the dividers 206 with identically charged electrodes 236 on both sides. That is to say, a divider of the dividers 206 with a portion of the substrate 240 comprising electrodes 236 in solid line comprises solid line electrodes and a heating element on first and second surfaces of the divider. As shown, the first and second surfaces face different compartments 209, and thus may experience different soot depositions. By positioning the sensor element 234 above the inner device 218, and therefore gap 226, issues of water droplets and larger contaminants impinging on the sensor element and causing fluctuations in the sensor output may be reduced. The description of the electric circuit and the composition of the sensor element and the substrate are common to FIG. 4.

Turning now to FIG. 3, a schematic view 300 shows exhaust flow through the PM sensor assembly 202. Specifically, view 300 depicts exhaust flowing into the PM sensor assembly 202 via the perforations 244 located adjacent the bottom end 270 of the outer device 216. Herein, the perforations 244 are configured to receive exhaust from the exhaust passage 210 and direct the exhaust into the interior flow space 242 formed inside the outer device 216. Directing the exhaust into the interior flow space 242 includes flowing exhaust gas in a radially inward direction relative to the outer device 216. The exhaust gas may enter the outer device 216 via any of the perforations 244. In one example, exhaust gas may readily flow through upstream facing perforations (e.g., perforations 244a and 244h) and enter the PM sensor assembly 202. Furthermore, exhaust gas may turn in a direction opposite to the direction of exhaust flow (indicated by arrows 258) to enter the PM sensor assembly 202 via downstream facing perforations (e.g., perforations 244d and 244e). Still further, exhaust gas may turn in a direction perpendicular to the direction of exhaust flow (arrows 258) via side facing perforations (e.g., perforations 244b, 244c, 244f, and 244g). It will be appreciated that, in some examples, more exhaust gas may enter the PM sensor assembly 202 via the perforations 244a and 244h compared to the other perforations. Additionally, larger or heavier contaminants and/or water droplets 274 (such as particulates having a larger than threshold size or weight) in the exhaust may only enter the PM sensor assembly via the upstream perforations 244a and 244h. As such, the larger contaminants and/or water droplets 274 may have a momentum too great to be able to turn around and enter the PM sensor assembly 202 via the side perforations and downstream perforations. This may reduce an amount of large particulates and/or water droplets from entering the PM sensor assembly 202. FIG. 3 shows a similar view of the sensor assembly 202 shown in FIG. 2. Thus, components may be similarly numbered in subsequent figures.

As shown, each of the perforations 244a, 244b, 244c, 244d, 244e, 244f, 244g, and 244h correspond to each of the compartments 209a, 209b, 209c, 209d, 209e, 209f, 209g, and 209h, respectively. As described above, each compartment is fluidly separated from the other compartments. Furthermore, each of the compartments is fluidly coupled with the dome 246. Thus, exhaust gas may flow from the compartment 209b, into the dome 246, and to the compartment 209g, where the exhaust gas flows back to the exhaust passage via the perforation 244g. In this way, exhaust may flow from any of the compartments 209 to the dome 246 and then into any of the compartments 209 from the dome 246.

As explained previously with reference to FIG. 2, the PM sensor assembly 202 is sealed expect for the perforations 244. In this way, the PM sensor assembly 202 comprises no other inlets or additional outlets other than the perforations 244. Therefore, exhaust gas in the PM sensor assembly flows back to the exhaust passage through either the perforation through which it entered the PM sensor assembly and/or through a different perforation. A general exhaust flow through the PM sensor assembly 202 may include exhaust gas flowing up toward the top end 260, through the dome 246, down toward the bottom end 270, and out of the PM sensor assembly 202 via a perforation of the perforations 244, as will be described below. It will be appreciated that exhaust gas flow into the PM sensor assembly 202 flow in a direction opposite to exhaust gas flow out of the PM sensor assembly 202.

An example exhaust gas flow is depicted, wherein exhaust gas enters the compartment 209a via the perforation 244a (as shown by arrow 278) in a radially inward direction relative to the outer device 216. The exhaust inside the interior flow space 242 is forced to travel toward the top end 260 of the PM sensor assembly 202. Specifically, the exhaust and the large particulates and/or water droplets flow in a direction perpendicular (as indicated by arrow 281 and solid black circles 274) to the direction of exhaust flow inside the exhaust passage 210 (as indicated by arrows 258). It will be appreciated that exhaust arrow 281 may also swirl and/or flow annularly within the compartment 209a, however, its general direction of flow is parallel to arrow 281 depicted in FIG. 3. The exhaust gas then flows through the annular space 224 between the outer 216 and inner 218 devices (shown by arrow 283) while the large particulates and/or water droplets 274 impinge onto the inner device 218. As described above, the annular space 224 may be too small for large particulates and/or water droplets to flow therethrough. Additionally or alternatively, the momentum of the large particulates and/or water droplets may force the large particulates and/or water droplets to flow adjacent the axial axis 298, where the inner device 218 is located.

Exhaust gas in the compartment 209a flows across surface of the sensor element 234 before flowing into the dome 246 (shown by arrow 284). Exhaust flow 284 may deposit particulates onto the substrate 240 before flowing into the dome 246. The particulates may electrically couple oppositely charged electrodes of the electrodes 236. As described above, each divider of the dividers comprises only a positive or negative electrode. Additionally, the dividers alternate such that adjacent dividers comprise oppositely charge electrodes. In this way, a compartment comprises at least one instance of a positive electrode and a negative electrode. For example, the compartment 209a is formed via two dividers of the dividers 206, wherein one divider is shown having a dashed line electrode and the other divider is shown having a solid line electrode. As particulates build up on the substrate 240 in the compartment 209a, the electrodes may become coupled, as will be described below. In some examples, only oppositely charged electrodes in a compartment may become electrically coupled. In other examples, oppositely charged electrodes of different compartments may become electrically coupled.

In some examples, the exhaust gas may collide with the top end 260 before following an outline of the top end 260 into the dome 246. Exhaust gas flows in an upward direction to enter the dome 246, since the dome is outside of the exhaust passage 210 and vertically above the PM sensor assembly 202, as described above. Exhaust gas in the dome may swirl around before exiting the dome 246 and entering any of the compartments 209. In one example, the exhaust gas in the dome 246 may be evenly split such that an even amount of exhaust gas enters each of the compartments 209. However, as shown by arrows 285, all of the exhaust gas exiting the dome 246 enters the compartment 209e.

Additionally, exhaust gas flowing into and out of the dome 246 flows passed the sensor element 234. The positioning of the sensor element 234 has several advantages.

Firstly, the sensor element 234 is positioned to sample exhaust gas from each of the compartments 209, which may improve an accuracy of measured PM. Secondly, the sensor element may receive even PM deposition due to the turbulence generated in the PM sensor assembly 202 by the inner device 218 and the dome 246. As a result, the sensor element 234 may accurately estimate PM in the exhaust flow.

Specifically, the exhaust inside compartment 209e flows downward in a direction orthogonal to arrows 258 and opposite arrow 281 (as indicated by arrow 286). Thus, exhaust gas flowing out of the dome 246 and into compartments 209 flows in a direction opposite a direction of arrows 281 and 283. That is to say, exhaust gas entering the compartment 209e from the exhaust passage 210 (not shown) flows in a direction opposite arrow 286. The exhaust flows through the annular space 224 between the outer 216 and inner 218 devices. Exhaust is then directed toward the bottom end 270, where it may turn and flow through the perforation 244e. Exhaust gas flowing through the perforation 244e flows in a direction parallel to the direction of exhaust gas flow in the exhaust passage 210 (arrows 258) as shown by arrows 287. The exhaust gas exiting the PM sensor assembly 202 combines with exhaust gas in the exhaust passage, indicated by arrows 258 and arrows 288. By doing this, exhaust gas flowing through downstream facing perforations (e.g., 244d and 244e) and into the exhaust passage 210 flows in a direction parallel to exhaust gas flow (arrows 258). Further, exhaust gas flowing through side facing perforations (e.g., 244b, 244c, 244f, and 244g) and into the exhaust passage 210 flows in a direction orthogonal to exhaust gas flow (arrows 258) before turning and flowing in a direction parallel to exhaust gas flow. Still further, exhaust gas flowing through upstream facing perforations (e.g., 244a and 244h) and into the exhaust passage 210 flows in a direction opposite to exhaust gas flow (arrows 258) before turning and flowing in a direction parallel to exhaust gas flow. In this way, the perforations 244 function as inlets and outlets of the PM sensor assembly 202.

To summarize, exhaust gas flows through one a perforation of the perforations located near a bottom end of the PM sensor assembly, where the exhaust gas enters a compartment of the internal flow space of the PM sensor assembly. The internal flow space is divided into a plurality of equally sized compartments fluidly separated from one another. As the exhaust gas flows up the compartment and around the internal device, it flows passed the sensor element and into a dome. Thus, the exhaust gas may deposit an amount of particulates onto a substrate of the sensor element before flowing into the dome, where the exhaust gas may be redirected to any of the compartments of the internal flow space. The exhaust gas flows in a downward direction, passing over the sensor element where the exhaust gas may again deposit particulates, and toward the bottom end of the PM sensor assembly. The exhaust gas flows out a perforation of the compartment in a radially outward direction relative to the exhaust passage.

In some examples, additionally or alternatively, a majority of exhaust gas may enter the PM sensor assembly via the upstream perforations and a majority of exhaust gas may exit the PM sensor assembly via the downstream perforations. With reference to FIG. 3, the upstream perforations are to a left of the axial axis and the downstream perforations are to a right of the axial axis. This may provide the PM sensor assembly with a substantially U-shaped exhaust gas flow. Thus, an example particulate matter sensor, comprising a pair of electrodes formed on first surfaces of a sensor element, a heating element formed on second surfaces of the sensor element, the second surface opposite the first surface, and a plurality of dividers dividing an interior flow space of the particulate matter sensor into equally sized compartments. Additionally or alternatively, each of the dividers is in face-sharing contact with the second surface of the sensor element, and where the first surface of the sensor element is exposed to the annular space. Additionally or alternatively, the dividers are impervious to exhaust gas flow, and where a number of dividers is equal to eight. Additionally or alternatively, each of the dividers corresponds to a positive or negative electrode of the sensor element, and where adjacent dividers correspond to different electrodes. Additionally or alternatively, the dividers are an eight-point star shape from a top-down view, symmetric about a center of the particulate matter sensor. Additionally or alternatively, each of the compartments comprises at least one perforation fluidly coupling the compartment to an exhaust passage. Additionally or alternatively, the electrodes comprise linear positive and linear negative electrodes, and where the positive and negative electrodes are located on alternating dividers. Additionally or alternatively, the dividers are located inside of an outer device, the dividers are physically coupled to the outer device along a long outer edge while being physically coupled to each other along a long inner edge, and where an inner device is mounted inside the outer device via the dividers.

Turning now to FIG. 4, a schematic view 400 of the sensor element 234 of FIG. 2 and an accompanying electric circuit 414 is shown. Specifically, electrodes 236 formed on a flat substrate 240 are shown. Since each of the dividers 206 are rectangular and abutted with one another along the axial axis 298 to divide the internal flow space evenly, the shape of the dividers 206 from a dome (e.g., dome 246 of FIGS. 2 and 3) is an eight-pointed star. Thus, it may be advantageous to include a square substrate for the sensor element to increase the surface area available for soot particulate adsorption. However, various other geometries of the substrate and the electrode layout may be possible without deviating from the scope of the present disclosure. Some example layouts include rectangular or circular substrate with interdigitated comb electrodes.

In view 400, the substrate 240 of the sensor element 234 is square with a length less than a radius $R_1$ of the dividers 206. The substrate 240 of the sensor element 234 may be manufactured from electrically insulating materials. Some examples of possible electrically insulating materials may include oxides such as alumina, zirconia, yttria, lanthanum oxide, silica, and combinations comprising at least one of the foregoing, or any like material capable of inhibiting electrical communication and providing physical protection for the electrodes 406 and 408. In some examples, the substrate 240 may be composed of a porous ceramic material (e.g., porosity of about 60%).

The sensor electrode 236 includes a pair of electrodes 406 and 408 formed on separate surfaces of the sensor element 234. Herein, the pair of electrodes 406 and 408 may form linear tines indicated by dotted and solid lines in view 400, respectively. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. Each electrode of the pair may be composed of the same or different material as the other electrode of the pair. For example, the electrode 406 may be composed of the same material as the electrode 408. In another example, electrode 406 and electrode 408 may be composed of different materials. The distance between the "tines" of the two electrodes may typically be in the range from 30 micrometers to 50 micrometers with the linewidth of each individual "tine" being about the same value, although the latter may be excluded. The distance may be measured from a first electrode of the electrodes 406, to the axial axis 298, and to a single electrode of the electrodes 408 adjacent the first electrode. As shown, the electrodes 406 and 408 alternate such that an electrode of the electrodes 408 is located between each of the electrodes 406.

The electrodes 406 and 408 may be connected via electrical connections to an electric circuit 414. The electrode 408 of the sensor element 234 is connected with connecting wire 412 to a positive terminal of a voltage source 416 of the electric circuit 414. Thus, the electrode 408 may be referred to as a positive electrode. Similarly, the electrode 406 of the sensor element 234 is connected to a measurement device 418 via a connecting wire 410, and further connected to a negative terminal of the voltage source 416 of the electric circuit 414. Thus, the electrode 406 may be referred to as a negative electrode. The interconnecting wires 410 and 412, the voltage source 416, and the measurement device 418 are part of the electric circuit 414 and are housed outside the exhaust passage 210 (as one example, <1 meter away). Further, the voltage source 416 and the measurement device 418 of the electric circuit 414 may be controlled by a controller, such as controller 12 of FIG. 1, so that particulate matter collected at the PM sensor assembly 202 may be used for diagnosing leaks in the DPF, for example. As such, the measurement device 418 may be any device capable of reading a resistance (or current) change across the electrodes, such as a voltmeter (or an ammeter). As PM or soot particles get deposited between the electrodes 406 and 408, the current measured between the electrodes 406 and 408 may start to increase, which is measured by the measurement device 418. The controller 12 may be able to determine the current and infer a corresponding PM or soot load on the electrodes 406 and 408 of the sensor element 234 of the PM sensor assembly (e.g., PM sensor assembly 202 of FIGS. 2 and 3). By monitoring the load on the sensor element 234, the exhaust soot load downstream of the DPF may be determined, and thereby used to diagnose and monitor the health and functioning of the DPF.

In view 400, electrode 406 includes a plurality of linear tines of equal length. The electrode 406 (interchangeably referred to as the negative electrode) includes a substantially straight portion 420 connecting the electrode 406 to the interconnecting wire 410. Herein, the straight portion 420 extends above the substrate 240. This forces the electrode 406 to extend above the substrate 240 as well, thereby preventing the electrode 406 from contacting the electrode 408. The electrode 406 is symmetric about the axial axis 298.

Similar to the negative electrode 406, the electrode 408 includes a plurality of linear tines of substantially equal length. The electrode 408 (interchangeably referred to as the positive electrode) includes a substantially straight portion 422 connecting the positive electrode 408 to the interconnecting wire 412. Herein, the straight portion 422 may be below the straight portion 420, following an outline of and sitting atop the substrate 240. That is to say, the straight portion 422 and electrode 408 are flush against the substrate 240 before reaching an end point of the substrate 240. Alternatively, the straight portion 420 and electrode 406 are spaced away from the substrate 240 before its end point to prevent contact between the electrodes 406 and 408. As an example, a length of the straight portion 422 of the positive electrode 408 may be equal to or lesser than or greater than the length of the straight portion 420 of the negative electrode 406. The positive electrode 408 is symmetric about the axial axis 298. Furthermore, the positive electrode 408 extends in directions oblique to the negative electrode 406. Specifically, an angle between the negative 406 and positive 408 electrodes is exactly 45°.

The heating element 238 is shown on a second surface of the substrate 240 in face-sharing contact with the dividers 206. Each divider of the dividers 206 is sandwiched by an innermost heating element layer, a middle substrate layer, and an outer electrode layer. The outer electrode layer of a divider comprises similarly charged electrode tines (e.g., either positive or negative). In this way, each compartment (e.g., compartments 209 of FIGS. 2 and 3) comprises positive 408 and negative 406 electrodes.

Figure 5:
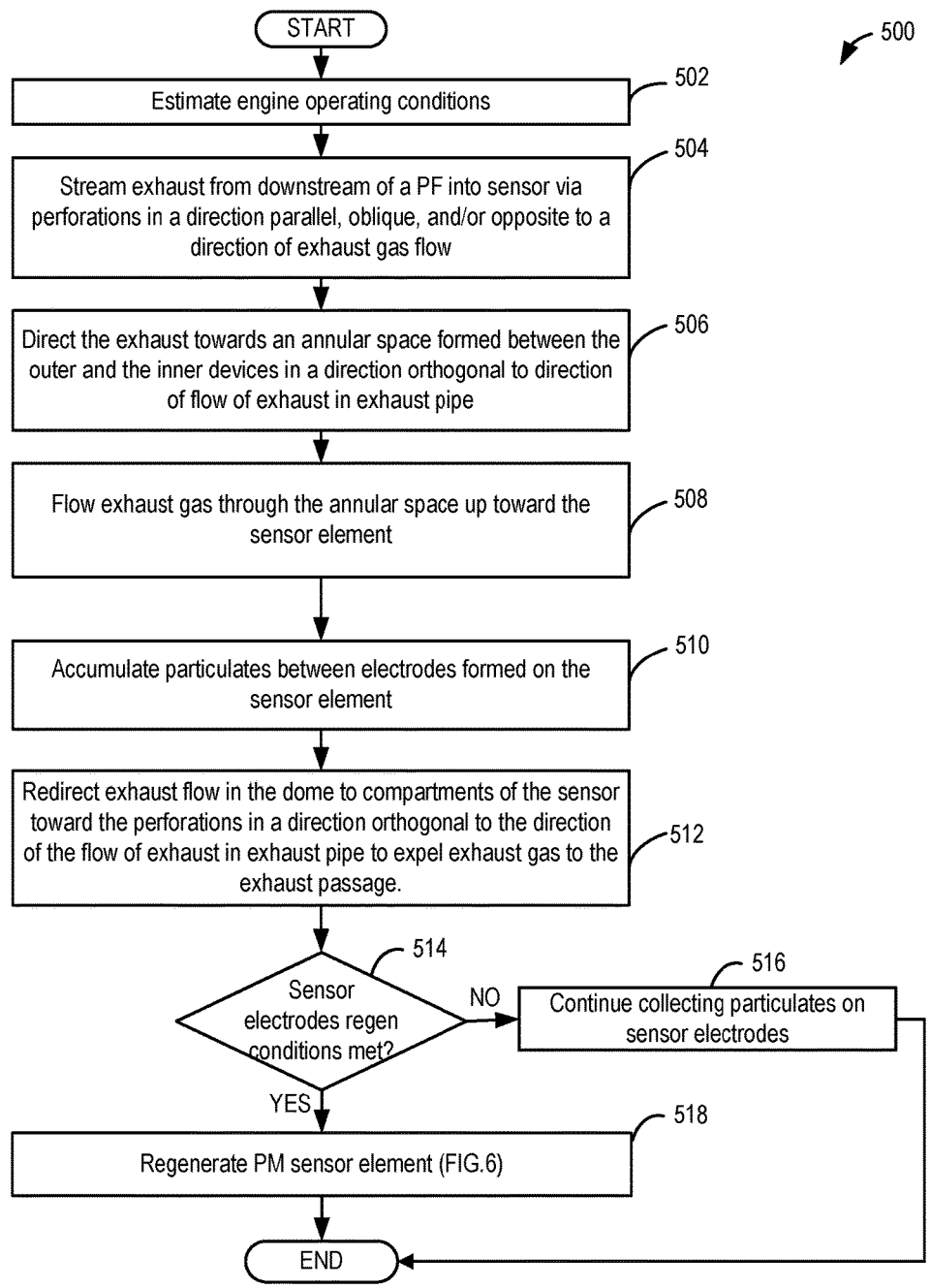
FIG. 5 shows a flow chart depicting an example method for accumulating particulates in the exhaust flow across the sensor element positioned within an inner device of the cylindrical assembly of the PM sensor.

Turning now to FIG. 5, a method 500 for accumulating particulates in the exhaust flow across sensor electrodes positioned within the PM sensor (such as a PM sensor 106 shown at FIG. 1, and/or PM sensor assembly 202 of FIG. 2, for example) is shown. Specifically, the particulates in the exhaust flow may be accumulated across electrodes formed on surfaces of the dividers positioned within a cylindrical assembly of the PM sensor. Herein, the cylindrical assembly includes an inner circular device positioned within an outer cylindrical device and separated by a gap. In addition, the cylindrical assembly includes a plurality of perforations to direct exhaust in and out of compartments of the cylindrical assembly.

Instructions for carrying out method 500 and the rest of the methods 600 and 700 included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 502, method 500 includes determining and/or estimating engine-operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

Method 500 proceeds to 504 where a portion of exhaust flowing from downstream of a particulate filter (such as DPF 102 of FIG. 1) is directed into a PM sensor via perforations. Herein, the perforations are circular and located adjacent to a bottom end of an outer device. As explained earlier, the perforations fluidly coupled the compartments of the interior flow space of the outer device to an exhaust passage. Thus, the perforations admit exhaust gas into the compartments. The direction of flow of exhaust through the perforations may be parallel to, oblique to, orthogonal to, and/or opposite to the direction of flow of exhaust inside the exhaust pipe, for example, as described above.

Next, method 500 proceeds to 506. At 506, method 500 includes directing the exhaust towards an annular space formed between the outer and the inner devices in a direction orthogonal to direction of flow of exhaust in exhaust passage. As described above, exhaust gas flows upward in a direction opposite gravity.

Method 500 proceeds to 508. At 508, method 500 includes flowing exhaust gas through the annular space toward the sensor element located adjacent the top end of the sensor. The sensor element is physically coupled to surfaces of the dividers, which separate the interior flow space of the outer device into substantially equally sized compartments. As described above, the heating element of the sensor element is pressed against surfaces of the dividers and the electrodes are exposed to exhaust gas in the compartments. Method 500 proceeds to 510.

At 510, method 500 includes accumulating particulates between electrodes formed on the sensor element. Specifically, at 510, particulates in the compartments adjacent the top end of the outer device are directed towards the electrodes of the sensor element and the particulates are deposited across the electrodes. The direction of exhaust flow in the compartments is orthogonal to the direction of exhaust flow inside the exhaust passage. As described previously, the sensor element including electrodes is positioned above the inner device. The positive electrodes are connected to the positive terminal of a voltage supply and the negative electrodes are connected to a measurement device and then to the negative terminal of the voltage supply. When the controller applies a voltage to the sensor electrodes, particulates inside the compartments may experience a strong electric field, enabling them to be accumulated between the electrodes. In addition, a load on the sensor electrodes is estimated based on a current generated in the sensor electrodes. When particulates accumulate on the surface of the sensor electrodes, the resistance of the electrodes starts decreasing and a current measured by the measurement device starts to increase. The controller may be able to deduce a load on the sensor electrodes based on the current measured across the electrodes. Method 500 then proceeds to 512.

At 512, method 500 includes redirecting exhaust flow in the dome to compartments of the sensor toward the perforations in a direction orthogonal to the direction of the flow of exhaust in exhaust pipe to expel exhaust gas to the exhaust passage. In some examples, a majority of exhaust gas may flow through the downstream perforations due to their lower static pressure and less exhaust gas entering the sensor via the downstream perforations. Method 500 then proceeds to 514.

At 514, method 500 includes intermittently checking if the sensor electrode has met the regeneration conditions. Specifically, when the soot load on the PM sensor is greater than the threshold, or when a resistance of the PM sensor (adjusted for temperature) drops to a threshold resistance, or when a current of the PM sensor is greater than a threshold current, PM sensor regeneration conditions may be considered met. In some examples, if a threshold time has elapsed since an immediately previous sensor regeneration, regeneration condition may be considered met. The PM sensor may demand regeneration to enable further PM detection.

Figure 6:
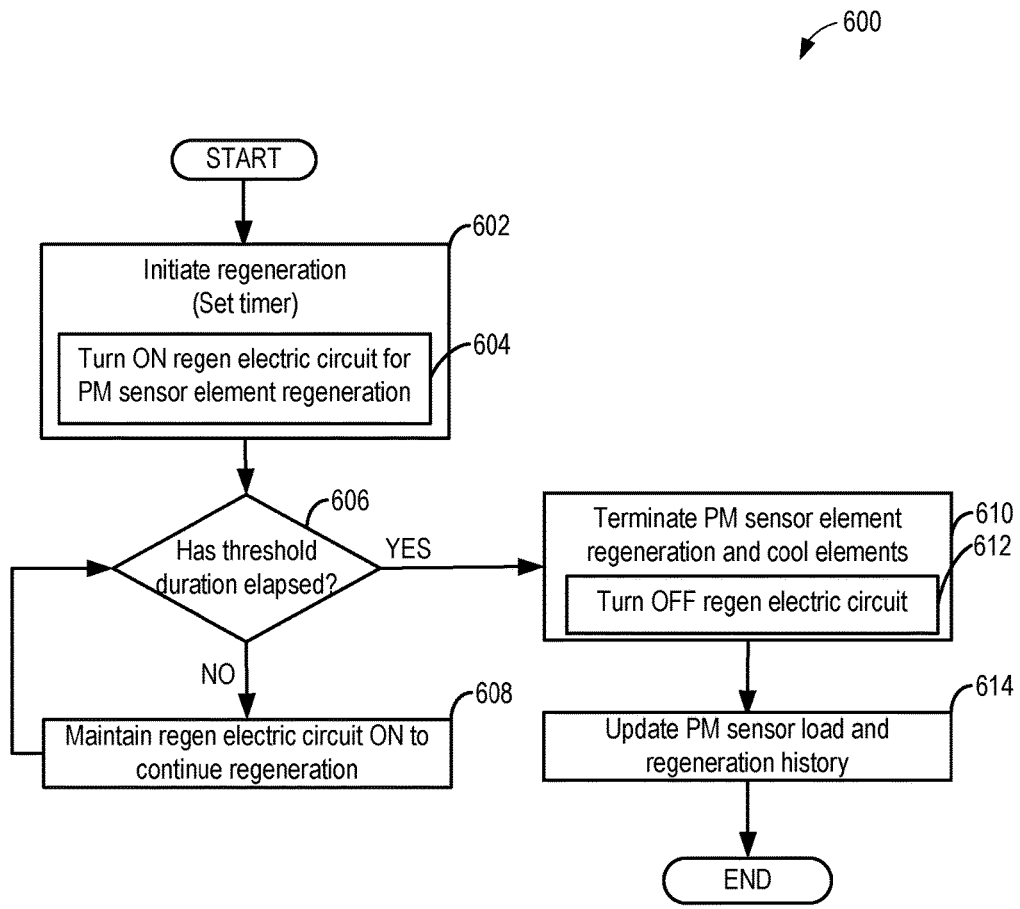
FIG. 6 is a flow chart depicting an example method for regenerating the sensor electrodes of the PM sensor.

If regeneration conditions are met (e.g., "YES" at 514), then method 500 proceeds to 518 where the PM sensor may be regenerated by performing a method described in FIG. 6. Briefly, regeneration of the PM sensor may be initiated by heating up the sensor. The PM sensor may be heated by actuating a heating element formed on a different surface of the sensor element that is opposite to the surface including the electrodes, for example. Herein, the controller may close the switch in a regeneration circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes. However, if PM sensor regeneration conditions are not met (e.g., "NO" at 514), then method proceeds to 516 where the particulates may continue to be collected on the sensor electrodes and the method ends.

Thus, an example method may include streaming exhaust from downstream of a particulate filter into an exhaust sensor assembly via perforations positioned adjacent a bottom end of an outer device in a direction radially inward to a center of the outer device, the perforations fluidly coupling compartments of the outer device to an exhaust passage and directing the exhaust towards an inner device located between the perforations and a sensor element, where the exhaust flows in a direction orthogonal to the flow of exhaust in the exhaust passage. Additionally or alternatively, the method further comprises flowing the exhaust gas through an annular space between the inner and outer devices toward the sensor element. Additionally or alternatively, the sensor element is adjacent a dome of the exhaust sensor assembly positioned outside of the exhaust passage, and where the dome is hollow and configured to direct exhaust gas to the compartments after flowing exhaust gas over the sensor element, where the exhaust flows in a direction orthogonal to the flow of exhaust in the exhaust passage. Additionally or alternatively, the exhaust sensor assembly comprises no other inlets or additional outlets other than the perforations.

Turning now to FIG. 6, a method 600 for regenerating the PM sensor (such as a PM sensor 106 shown at FIG. 1, and/or PM sensor assembly 202 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may demand regeneration to enable further PM detection. At 602, regeneration of the PM sensor may be initiated and the PM sensor may be regenerated by heating up the sensor at 604. The PM sensor may be heated by actuating a heating element until the soot load of the sensor has been sufficiently reduced by oxidation of the carbon particles between the electrodes.

The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration and the method ends. The method 600 may return to 606 to continue to monitor if the threshold duration has elapsed. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

In some examples, additionally or alternatively, the controller (e.g., controller 12 of FIG. 1) may determine which electrodes of the positive and negative electrodes are electrically coupled. For example, only the electrodes in a single compartment may be electrically coupled. As such, heating elements corresponding to only the single compartment may be activated. In this way, heating elements of the sensor element may be individually operated to reduce power consumption during PM sensor element regenerations. In other embodiments, the PM sensor assembly may be rotated via a motor. This may adjust an amount of exhaust gas entering the compartments (e.g., more exhaust gas enters upstream compartments compared to downstream compartments). Thus, the PM sensor assembly regeneration may include rotating the PM sensor assembly such that fully loaded compartments demanding regeneration may be rotated to a more downstream position to decrease an amount of exhaust gas flowing into the fully loaded compartments.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine-operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
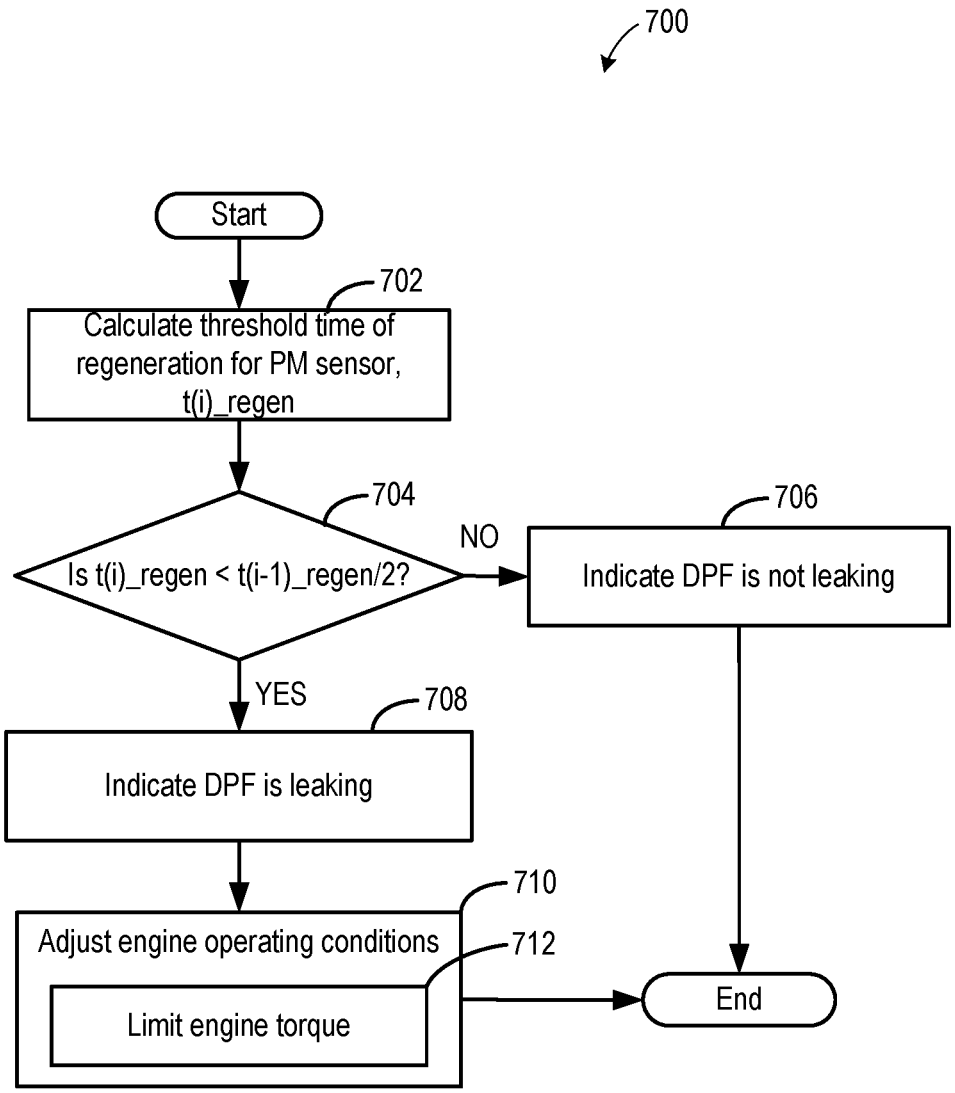
FIG. 7 shows a flow chart depicting an example method for diagnosing leaks in a particulate filter positioned upstream of the PM sensor.
Figure 8:
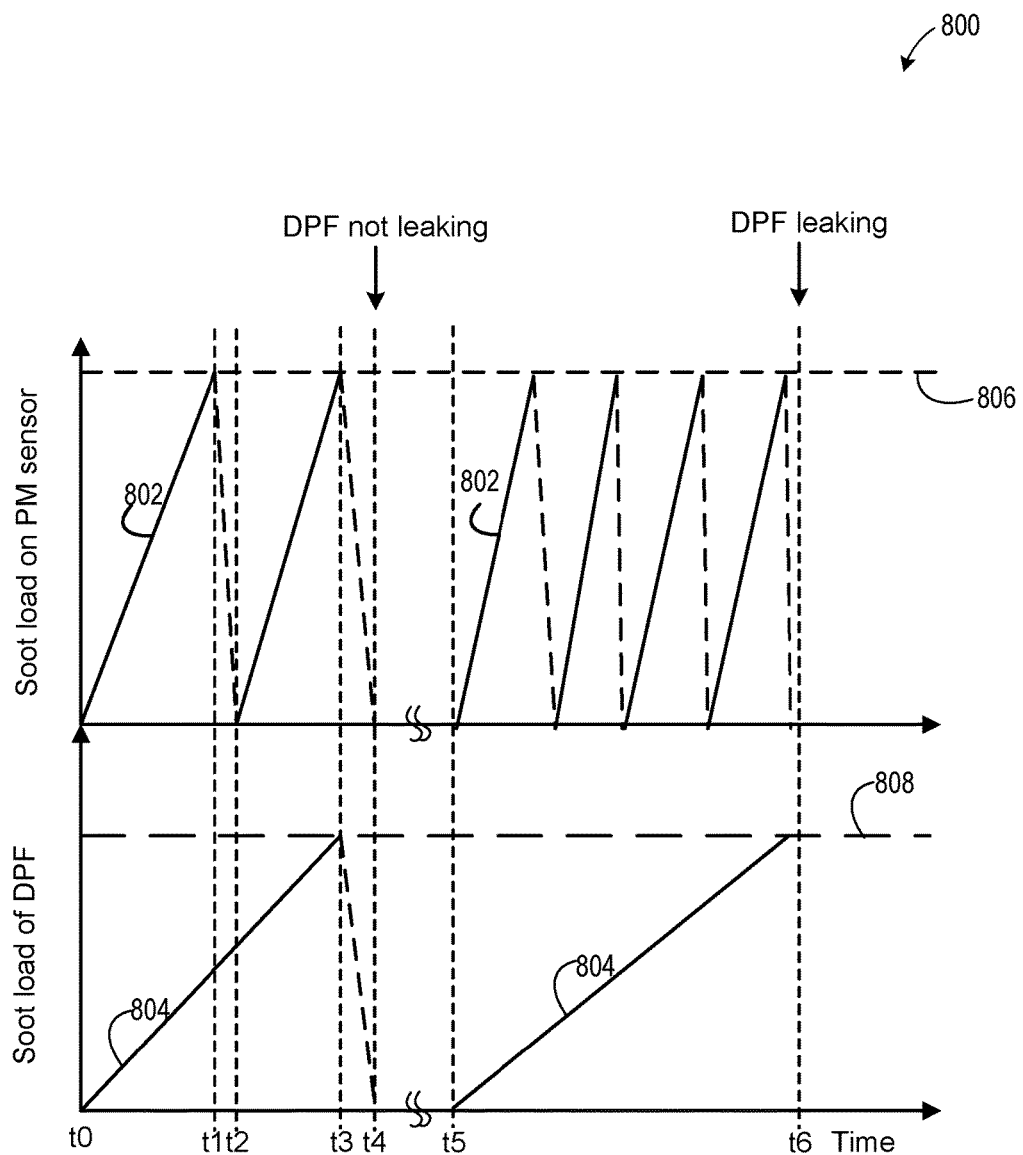
FIG. 8 shows an example relationship between a soot load on the PM sensor, and a soot load on a particulate filter positioned upstream of the PM sensor.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5, and t6 identify significant times in the operation and system of PM sensor and DPF.

The first plot of FIG. 8 shows a soot load on the PM sensor. As previously described, PM gets deposited across the positive and negative electrodes formed on a cylindrical substrate that is positioned inside an inner device closer to a hole formed at the bottom of the inner device, for example. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, as PM continues to accumulate, the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may demand regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804) reaches the threshold soot load for DPF regeneration (marker 808). Between t3 and t4, the DPF may be regenerated to burn off the soot deposited on the DPF. Further at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended.

In this way, a sensor element may be shielded by one or more cylindrical protection tubes and circular plate. Exhaust gases may enter the sensor assembly via perforations located near a bottom end of the cylindrical protection tube. As such, the exhaust may undergo changes in flow direction which helps reduce flow rate. In addition, water droplets and large contaminants flow into the circular plate located inside the cylindrical protection tube between the sensor element and the perforations. The exhaust gas flows through the compartments to the sensor element and a dome positioned outside of the exhaust passage. The dome receives exhaust gas and redistributes the exhaust gas to the compartments. Exhaust gas then flows back through the compartments toward the perforations. As such, exhaust gas entering the cylindrical protection tube flows along a length of its compartments twice. In this way, by separating the perforations from the sensor element with the circular plate, issues of uneven soot deposition may be prevented due to the even flow induced by the annular space.

A technical effect of greater uniform flow impingement of sample gasses on a particulate matter sensor may be achieved by decreasing the flow speed of the exhaust gas. By interrupting the flow path of the exhaust gas, and decreasing its speed, the uniformity of the flow on the particulate matter sensor surface may be increased. Further still, by positioning the sensor element below the dome, exhaust gas is forced to flow passed the sensor element twice before it is expelled from the cylindrical protection tube.

A particulate matter sensor assembly comprising a cylindrical assembly, an inner device positioned within an outer device of the cylindrical assembly with a radius less than a radius of the outer device, and a sensor element located above an annular space proximal to a dome located at a top end of the outer device. A first example of the sensor further includes where the annular space is a portion of an interior flow space of the outer device located between the outer and inner devices. A second example of the sensor, optionally including the first example, further includes where the interior flow space is divided into identical compartments via a plurality of solid dividers impervious to exhaust gas flow, and where each of the compartments comprises a perforation for receiving and expelling exhaust gas. A third example of the sensor, optionally including the first and/or second examples, further includes where the dome is fluidly coupled to the interior flow space of each of the compartments. A fourth example of the sensor, optionally including one or more of the first through third examples, further includes where the dome extends outside of an exhaust pipe of an exhaust passage. A fifth example of the sensor, optionally including one or more of the first through fourth examples, further includes where the inner device prevents large particulates and water droplets from flowing to the sensor element. A sixth example of the sensor, optionally including one or more of the first through fifth examples, further includes where the outer device comprises a plurality of perforations located along a common plane facing radially outward directions. A seventh example of the sensor, optionally including one or more of the first through sixth examples, further includes where the inner device is completely spaced away from and suspended within the outer device, and where the outer device is a cylinder shape and the inner device is a circular shape.

A particulate matter sensor comprising a pair of electrodes formed on a first surface of a sensor element, a heating element formed on a second surface of the sensor element, the second surface opposite the first surface, and a plurality of dividers dividing an interior flow space of the particulate matter sensor into equally sized compartments. A first example of the sensor, further includes where each of the dividers is in face-sharing contact with the second surface of the sensor element, and where the first surface of the sensor element is exposed to the interior flow space. A second example of the sensor, optionally including the first example, further includes where the dividers are impervious to exhaust gas flow, and where a number of dividers is equal to eight. A third example of the sensor, optionally including the first and/or second examples, further includes where each of the dividers corresponds to a positive or negative electrode of the sensor element, and where adjacent dividers comprise oppositely charged electrodes. A fourth example of the sensor, optionally including one or more of the first through third examples, further includes where the dividers are an eight-point star shape from a top-down view, symmetric about a center of the particulate matter sensor. A fifth example of the sensor, optionally including one or more of the first through fourth examples, further includes where each of the compartments comprises at least one perforation fluidly coupling the compartment to an exhaust passage. A sixth example of the sensor, optionally including one or more of the first through fifth examples, further includes where the electrodes comprise linear positive and linear negative electrodes, and where the positive and negative electrodes are located on different dividers. A seventh examples of the sensor, optionally including one or more of the first through sixth examples, further includes where the dividers are located inside of an outer device, the dividers are physically coupled to the outer device along an outer edge while being physically coupled to each other along an inner edge, and where an inner device is mounted inside the outer device via the dividers.

A method, comprising streaming exhaust from downstream of a particulate filter into an exhaust sensor assembly via perforations positioned adjacent a bottom end of an outer device in a direction radially inward to a center of the outer device, the perforations fluidly coupling compartments of the outer device to an exhaust passage and directing the exhaust towards an inner device located between the perforations and a sensor element, where the exhaust flows in a direction orthogonal to the flow of exhaust in the exhaust passage. A first example of the method further includes flowing the exhaust gas through an annular space between the inner and outer devices toward the sensor element. A second example of the method, optionally including the first example, further includes where the sensor element is adjacent a dome of the exhaust sensor assembly positioned outside of the exhaust passage, and where the dome is hollow and configured to direct exhaust gas to the compartments after flowing exhaust gas over the sensor element, where the exhaust flows in a direction orthogonal to the flow of exhaust in the exhaust passage. A third example of the method, optionally including the first and/or second examples, further includes where the exhaust sensor assembly comprises no other inlets or additional outlets other than the perforations.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
   streaming exhaust from downstream of a particulate filter into an exhaust sensor assembly via perforations positioned adjacent a bottom end of an outer device in a direction radially inward to a center of the outer device, the perforations fluidly coupling compartments of the outer device to an exhaust passage;
   directing the exhaust towards an inner device located between the perforations and a sensor element, where the exhaust flows in a direction orthogonal to a flow of exhaust in the exhaust passage;
   directing the exhaust past the inner device, over the sensor element, and into a dome of the exhaust sensor assembly; and then
   directing the exhaust from the dome to the sensor element again.

2. The method of claim 1, wherein directing the exhaust towards the inner device includes flowing the exhaust through an annular space between the inner and outer devices.

3. The method of claim 1, wherein the sensor element is adjacent the dome of the exhaust sensor assembly, the dome positioned outside of the exhaust passage, where the dome is hollow, and further directs the exhaust to the compartments after flowing the exhaust over the sensor element, where the exhaust flows in the direction orthogonal to the flow of exhaust in the exhaust passage; and wherein a pair of electrodes is formed on a first surface of the sensor element, and a heating element is formed on a second surface of the sensor element.

4. The method of claim 1, wherein the exhaust sensor assembly comprises no other inlets or additional outlets other than the perforations.

5. The method of claim 1, further comprising, after directing the exhaust to the sensor element again, further directing the exhaust out of the exhaust sensor assembly and into the exhaust passage.

6. The method of claim 1, wherein the exhaust deposits particulates onto a substrate of the sensor element before being directed into the dome.

7. The method of claim 6, wherein the exhaust deposits further particulates onto the substrate of the sensor element when the exhaust is directed from the dome to the sensor element again.

8. A method, comprising:
   streaming exhaust from downstream of a particulate filter into an exhaust sensor assembly via perforations positioned adjacent a bottom end of an outer device in a direction radially inward to a center of the outer device, the perforations fluidly coupling compartments of the outer device to an exhaust passage; and directing the exhaust towards an inner device located between the perforations and a sensor element, where the exhaust flows in a direction orthogonal to a flow of exhaust in the exhaust passage, wherein the sensor element is adjacent a dome of the exhaust sensor assembly positioned outside of the exhaust passage, where the dome is hollow and configured to direct the exhaust to the compartments after flowing the exhaust over the sensor element, where the exhaust flows in the direction orthogonal to the flow of exhaust in the exhaust passage; and wherein a pair of electrodes is formed on a first surface of the sensor element, and a heating element is formed on a second surface of the sensor element.

9. The method of claim 8, wherein the dome is a hollow half-sphere.

10. The method of claim 8, further comprising flowing the exhaust through an annular space between the inner and outer devices toward the sensor element.

11. The method of claim 10, wherein flowing the exhaust toward the sensor element includes flowing the exhaust in an upward direction.

\* \* \* \* \*